United States Patent
Leppäluoto et al.

(10) Patent No.: US 11,804,290 B2
(45) Date of Patent: Oct. 31, 2023

(54) METHODS AND DEVICE ARRANGEMENT FOR PHYSICAL ACTIVITY THRESHOLDS REDUCING RISKS OF DIABETES, CARDIOVASCULAR DISEASES, INFLAMMATIONS, DEMENTIA, CANCERS AND MORTALITY IN SEDENTARY SUBJECTS

(71) Applicant: Gleap Health Technologies Oy, Hamina (FI)

(72) Inventors: Juhani Leppäluoto, Oulu (FI); Sirkka Keinänen-Kiukaanniemi, Oulu (FI); Timo Jämsä, Oulu (FI); Jari Jokelainen, Oulu (FI); Karl-Heinz Herzig, Oulu (FI)

(73) Assignee: Gleap Health Technologies Oy, Hamina (FI)

( * ) Notice: Subject to any disclaimer, the term of this patent is extended or adjusted under 35 U.S.C. 154(b) by 513 days.

(21) Appl. No.: 16/641,433

(22) PCT Filed: Aug. 29, 2018

(86) PCT No.: PCT/FI2018/050610
§ 371 (c)(1),
(2) Date: Feb. 24, 2020

(87) PCT Pub. No.: WO2019/043292
PCT Pub. Date: Mar. 7, 2019

(65) Prior Publication Data
US 2020/0202995 A1 Jun. 25, 2020

(30) Foreign Application Priority Data
Aug. 29, 2017 (FI) ...................................... 20177098

(51) Int. Cl.
*G16H 20/30* (2018.01)
*G16H 40/60* (2018.01)

(52) U.S. Cl.
CPC ............. *G16H 20/30* (2018.01); *G16H 40/60* (2018.01)

(58) Field of Classification Search
CPC ....................................................... G16H 40/60
See application file for complete search history.

(56) References Cited

U.S. PATENT DOCUMENTS 9,370,691 B2 * 6/2016 Nissila ............... A63B 24/0062
10,388,414 B2 8/2019 Otvos et al.
(Continued)

FOREIGN PATENT DOCUMENTS

CN 104520699 A 4/2015
JP 2010148884 A 7/2010
(Continued)

OTHER PUBLICATIONS

Mann et al. "Differential Effects of Aerobic Exercise, Resistance Training and Combined Exercise Modalities on Cholesterol and the Lipid Profile: Review, Synthesis and Recommendations," 2014 (Year: 2014).*

(Continued)

*Primary Examiner* — Aryan E Weisenfeld
(74) *Attorney, Agent, or Firm* — Meunier Carlin & Curfman LLC

(57) ABSTRACT

Highblood levels of very low density lipoprotein lipids (VLDLs) and glycoprotein acyl (Glyc A) are known to increase risk of diabetes, cardiovascular diseases, inflammations, cognitive impairments, cancers and premature deaths in sedentary persons. The invention determines physical activity thresholds of daily steps and accelerations to reduce plasma concentrations of VLDLs and Glyc A. The (Continued)

method and device is an accelerometer recording and classifying numbers of steps and accelerations and comparing the person's steps and accelerations with those shown to reduce VLDLs and Gly A. The invention is characterized in that if the daily number of accleration maxima exceeds the given en threshold of 2980 steps in the acceleration range 1.3-1.7 g, the person has performed physical activity, typically known to reduce circulating VLDLs and Glyc A.

6 Claims, 4 Drawing Sheets

(56) References Cited

U.S. PATENT DOCUMENTS

| | | |
|---|---|---|
| 2008/0312560 A1 | 12/2008 | Jämsen et al. |
| 2010/0098705 A1 | 4/2010 | Eugen-Olsen et al. |
| 2010/0137107 A1 | 6/2010 | Jämsäet al. |
| 2016/0077116 A1 | 3/2016 | Otvos et al. |
| 2016/0283696 A1 | 9/2016 | Leppäluoto et al. |

FOREIGN PATENT DOCUMENTS

| | | | | |
|---|---|---|---|---|
| WO | 2005/117703 A1 | 12/2005 | | |
| WO | 2013/080109 A2 | 6/2013 | | |
| WO | 2013/0184483 A1 | 12/2013 | | |
| WO | 2013/185014 A1 | 12/2013 | | |
| WO | WO2015/063366 | * | 5/2015 | ............ G01P 15/00 |

OTHER PUBLICATIONS

Vainiopää, A. et al., "Effects of Impact Exercise on Physical Performance and Cardiovascular Risk Factors", Medicine & Science in Sports & Exercise, 2007, pp. 756-763.
Herzig, K-H et al., "Light physical activity determined by a motion sensor decreases insulin resistance, improves lipid homeostasis and reduces visceral fat in high-risk subjects: PreDiabEx study RCT", International Journal of Obesity, 2014, vol. 38, No. 8, pp. 1089-1096.
Troiano, R. P. et al., "Physical Activity in the United States Measured by Accelerometer", Medicine & Science in Sports & Excercise, Feb. 2008, pp. 181-188.
Engström, G. et al., "Inflammation-Sensitive Plasma Proteins, Diabetes, and Mortality and Incidence of Myocardial Infarction and Stroke: A Population-Based Study", Circulation, 2003, vol. 52, pp. 442-447.
Bruno, A. et al., The Proangiogenic Phenotype of Natural Killer Cells in Patients with Non-Small Cell Lung Cancer1,2, Neoplasia, Feb. 2013, vol. 15, No. 2, pp. 133-142.
Carriere, I. et al., "Biomarkers of inflammation and malnutrion associated with early death in healthy elderly people", J Am Geriatr Soc., 2008, 56(5), pp. 840-846.
Svendstrup, M. et al., "Increased orosomucoid in urine is an independent predictor of cardiovascular and all-cause mortality in patients with type 2 diabetes at 10 years of follow-up", Journal of Diabetes and Its Complications, 2013, vol. 27, pp. 570-575.
Fischer, K. et al., "Biomarker Profiling by Nuclear Magnetic Resonance Spectroscopy for the Prediction of All-Cause Mortality: An Observational Study of 17,345 Persons", PLoS Medicine, 2014, 11(2): e1001606, 20 pages. doi: 10.1371/journal.pmed-1001606.
Rithchie, S. C. et al., "The Biomarker GlycA Is Associated with Chronic Inflammation and Predicts Long-Term Risk of Severe Infection", Cell Systems, 2015, vol. 1, pp. 293-301.
Cohen Manheim, I. et al., "Increase in the Inflammatory Marker GlycA over 13 Years in Young Adults Is Associated with Poorer Cognitive Function in Midlife", PLOS ONE, 2015, 15 pages. doi: 10.1371/journal.pone.0138036.
Festa, A. et al., "Nuclear Magnetic Resonance Lipoprotein Abnormalities in Prediabetic Subjects in the Insulin Resistance Atherosclerosis Study", Circulation, 2005, vol. 111, pp. 3465-3472.
Garvey, T. W. et al.,"Effect of Insulin Resistance and Type 2 Diabetes on Lipoprotein Subclass Particle Size and Concentration Determined by Nuclear Magnetic Resonance", Diabetes, 2003, vol. 52, pp. 453-462.
Goff, D. C. et al., "Insulin resistance and adiposity influence lipoprotein size and subclass concentrations. Results from the Insulin Resistance Atherclerosis Study", Metabolism, 2005, vol. 54, Issue 2, pp. 264-270.
Mora, S. et al., "Lipoprotein Particle Size and Concentration by Nuclear Magnetic Resonance and Incident Type 2 Diabetes in Women", Diabetes, 2010, vol. 59, pp. 1153-1160.
Kraus, W. E. et al., "Effects of the Amount and Intensity of Exercise on Plasma Lipoproteins", The New England Journal of Medicine, 2002, vol. 347, No. 19, pp. 1483-1492.
Brown, A. J. et al., "Effects of Exercise on Lipoprotein Particles in Women with Polycystic Ovary Syndrome", Med Sci Sports Exerc., 2009, 41(3), pp. 497-504. doi: 10.1249/NSS,0b013e31818c6c0c.
Halverstad, A. et al., "Endurance exercise training raises high-density lipoprotein cholesterol and lowers small low-density lipoprotein and very low-density lipoprotein independent of body fat phenotypes in older men and women", Metabolism, 2007, vol. 56, Issue 4, pp. 444-450.
Kujala, U. M. et al., "Long-term Leisure-time Physical Activity and Serum Metabolome", Circulation, 2013, vol. 127, pp. 340-348.
Herzig, K-H et al: "Low level activity thresholds for changes in NMR biomarkers and genes in high risk subjects for Type 2 Diabetes", Scientific Reports, 2017, vol. 7, No. 1, 10 pages. doi: 10.1038/s41598-017-09573-6.
Vainionpää, A. et al., "Intensity of exercise is associated with bone density change in premenopausal women", Osteoporos Int, 2006, vol. 17, pp. 455-463.
Japanese Office Action, Application No. 2020-53367, dated Aug. 2, 2022.
Chinese Office Action, Application No. 201880056039.1, dated Jan. 11, 2023.

* cited by examiner

METHODS AND DEVICE ARRANGEMENT FOR PHYSICAL ACTIVITY THRESHOLDS REDUCING RISKS OF DIABETES, CARDIOVASCULAR DISEASES, INFLAMMATIONS, DEMENTIA, CANCERS AND MORTALITY IN SEDENTARY SUBJECTS

PRIORITY

This application is a U.S. national application of the international application number PCT/FI2018/050610 filed on Aug. 29, 2018, which claims priority of Finnish application FI20177098 filed on Aug. 29, 2017, the contents of all of which are incorporated herein by reference.

The invention relates to a method and device for determining physical activity thresholds exceeding of which reduce risks for diabetes, cardiovascular diseases, inflammations, cognitive impairments, cancers and mortality in subjects who have sedentary lifestyle. The use of motion sensors and transduction units to measure physical activity volume and intensity have been presented in US2008/0312560A1 and in US 2010/0137107 A1.

The invention described here belongs to the medical discipline and includes the determination of physical activity thresholds that can be used in sedentary subjects for preventing risks for diabetes, cardiovascular diseases, inflammations, cognitive impairments, cancer and premature mortality by reducing glycoprotein acetylation (Glyc A) and very low density lipoprotein particles (VLDLs). The earlier invention related to physical activity reducing blood cholesterol (US 2010/0137107 A1) purposed for healthy subjects (Vainiopää et al. Med Sci Sports Exerc 2007) is not suitable to subjects who have sedentary lifestyle as they are not capable to perform prescribed physical activity previously shown to reduce blood cholesterol in healthy subjects (Herzig et al. Int J Obesity 2014). It should also be noted that subjects having sedentary lifestyle are unable to meet the current WHO guidelines for maintaining health and reducing health risks (Troiano et al. 2008).

THE BACKGROUND OF THE INVENTION

Sedentary lifestyle is increasingly common in industrialized countries in which energy rich diets are widely used and energy expenditure remains low. According to the WHO statistics over 1,400,000,000 of the world population are overweight or obese. Overweight and low physical activity result in an increase in the prevalence of several metabolic diseases mainly diabetes, cardiovascular diseases, inflammations, dementia, cancers, dementia and premature mortality. It is currently estimated that 500,000,000 of the population suffer from type 2 diabetes and the number will be doubled by the year 2030. In addition atherosclerosis, calcification of blood vessels, due to sedentary lifestyle exposes to deaths for cardiovascular diseases being the most frequent death causes in industrialized countries. The dead roll is presently 15,000,000 annually and is growing every year. Dementia relates also to sedentary lifestyle and according to WHO statistics we have today 40,000,000 people with dementia worldwide and the number is estimated to increase to 131,000,000 by the year 2050. Low levels of physical activity is also a dangerous risk factor disability-adjusted life years. According to the present WHO statistics it is annually responsible for 1,000,000 death cases and loss of 8,000,000 disability-adjusted life years.

The current physical activity recommendations of WHO, American Diabetes Association and American Heart Association state that healthy adults should perform at least 150 min moderate intensity physical activity every week such as walking at the speed of 5 km/h. The two thresholds time and walking speeds given in the guidelines should imply walking daily 2 km or 2000-3000 steps (depending on step lengths) within 21 min. These recommendations have been developed by reviewing subjects about their physical activity levels and demonstrated that about 50% of the adult population met the guidelines. Later physical activity levels have been studied objectively by accelerometers and the results showed that only less than 5% of the adult population was able to meet the above-mentioned official guidelines of physical activity. Therefore all the previous studies about physical activity using personal reviews or questionnaires overestimate health status and do not reveal the large occurrence of sedentary lifestyle in the present populations.

Novel biomarkers have been identified in body fluids by nuclear magnetic techniques and measured in healthy and diseased populations. Elevated concentrations of glycoprotein acetylation (GlycA) and low density lipoprotein particles (VLDLs) have been observed to associate with chronic diseases and mortality. High blood GlycA was found to relate to cardiac events and to increase mortality risk by 300% in healthy adult men (Engström et al. 2002) and to lead to premature death in patients suffering from lung cancer (Bruno et al 2013). In healthy elderly men and women high GlycA associated with early death (Carriere et al. 2008). High concentrations of GlycA in blood and urinary predict diabetes and mortality (Svendstrup et al. 2013). In a large population GlycA was measured and health status was followed for 5 years (Fischer et al. 2014). It was observed that high GlycA levels associated with cardiovascular diseases, cancer and mortality. High blood GlycA has also been found to be associated with bacterial sepsis, pneumonia and influenza (Rithchie et al. 2016). Many inflammatory markers were measured from young subjects and after 13 years high GlycA levels were found to be associated with global cognitive impairment (Cohen Manheim et al. 2015).

VLDL molecules carry blood lipids and their high concentrations have been found to relate to diabetes, cardiovascular disease and early deaths (Festa ey al. Garvey et al. 2003, Goff et al. 2005, Mora et al. 2010). High VLDL markers increase the diabetes risk by 400% (Mora tm. 2010) and with GlycA mortality risk twofold Fischer et al. 2014).

Effects of exercise interventions on biomarkers have been observed to reduce concentrations of circulating VLDL molecules in healthy men and women (Kraus et al. 2002, Brown et al. 2009) and in women suffering from polycystic ovarian disease (Halverstad et al. 2007). In corollary to this persistently physically active individuals had lower levels of VLDL molecules and GlycA than sedentary individuals (Kujala et al. 2013). Since high levels of GlycA and VLDLs present significant risks for diabetes, cardiovascular diseases, inflammation, dementia and cancer and predict early deaths and since regular exercises and physical activities reduce circulating levels of GlycA and VLDLs it is possible to tailor interventions for reducing the levels of these biomarkers.

The results of scientific studies demonstrate that increased physical activity is effective in preventing risk factors of diabetes, cardiovascular diseases, inflammations, dementia, cancers and early death in healthy and sedentary subjects. However, in none of these above-cited or other previous studies the exact amounts and intensities of physical activity preventing diabetes, cardiovascular diseases, inflammations, cancer or premature mortality have been described.

BRIEF DESCRITPION OF THE DRAWINGS

FIG. 1 shows results of eperiments where blood samples were taken at the beginning and end of the trial to measure blood GlycA and VLDLs by an NMR method. The VLDLs measured in this invention are VLDL triglycerides (VLDL TG), medium size VLDL particles (M VLDL P), extra large VLDL particles (XL VLDL P), extremely large VLDL triglycerides (XXL VLDL TG, see FIG. 1). The steps in the acceleration class 1.3-1.7 were divided by their magnitudes to quartiles. The changes during 3 months in GlycA and VLDLs concentrations within each quartile were analyzed and were in first quartile (below 2890 daily steps) significantly higher than in the other quartiles. Therefore 2890 daily steps at 1.3-1.7 g are the thresholds for physical activity, the exceeding of which significantly reduces blood GlycA and VLDLs.

PURPOSE OF THE INTERVENTION

High occurrence of chronic diseases and early deaths in the sedentary populations are major health problems and associate with high levels of GlycA and VLDLs. Regular physical activities are known to reduce high GlycA and VLDLs, but presently no physical activity guidelines are available to reduce these risk factors. It is our purpose to offer exact information about amounts and intensities of physical activity reducing blood GlyA and VLDLs and risks of diabetes, cardiovascular diseases inflammations, dementia, cancers and premature deaths. In order to achieve our purpose we registered physical activities and measured blood biomarkers in sedentary and active subjects and determined amounts and intensities of physical activities reducing GlycA and VLDLs concentrations. Our invention determines for the first time in sedentary subjects the thresholds of the amount and intensity of the physical activity reducing blood GlycA and VLDLs and risks of diabetes, cardiovascular diseases, inflammations, cancers and premature deaths.

THE METHODS OF THE INVENTION

Figure 2:
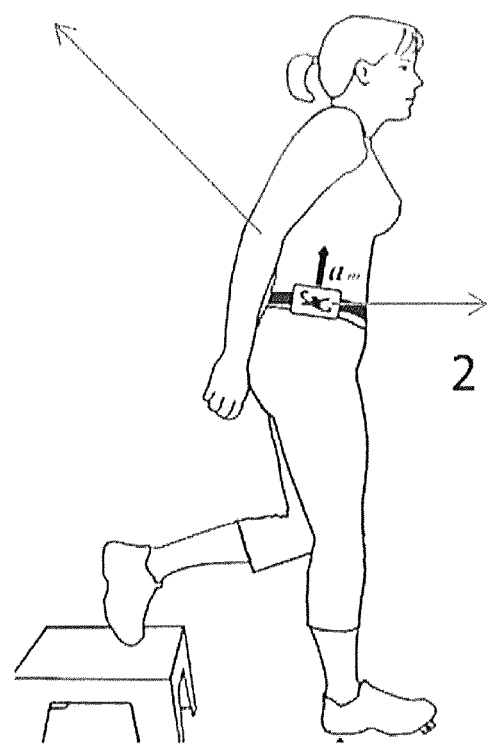
FIG. 2 shows a test person carrying a transducer unit on her waist to register acclerations of the body.
Figure 3:
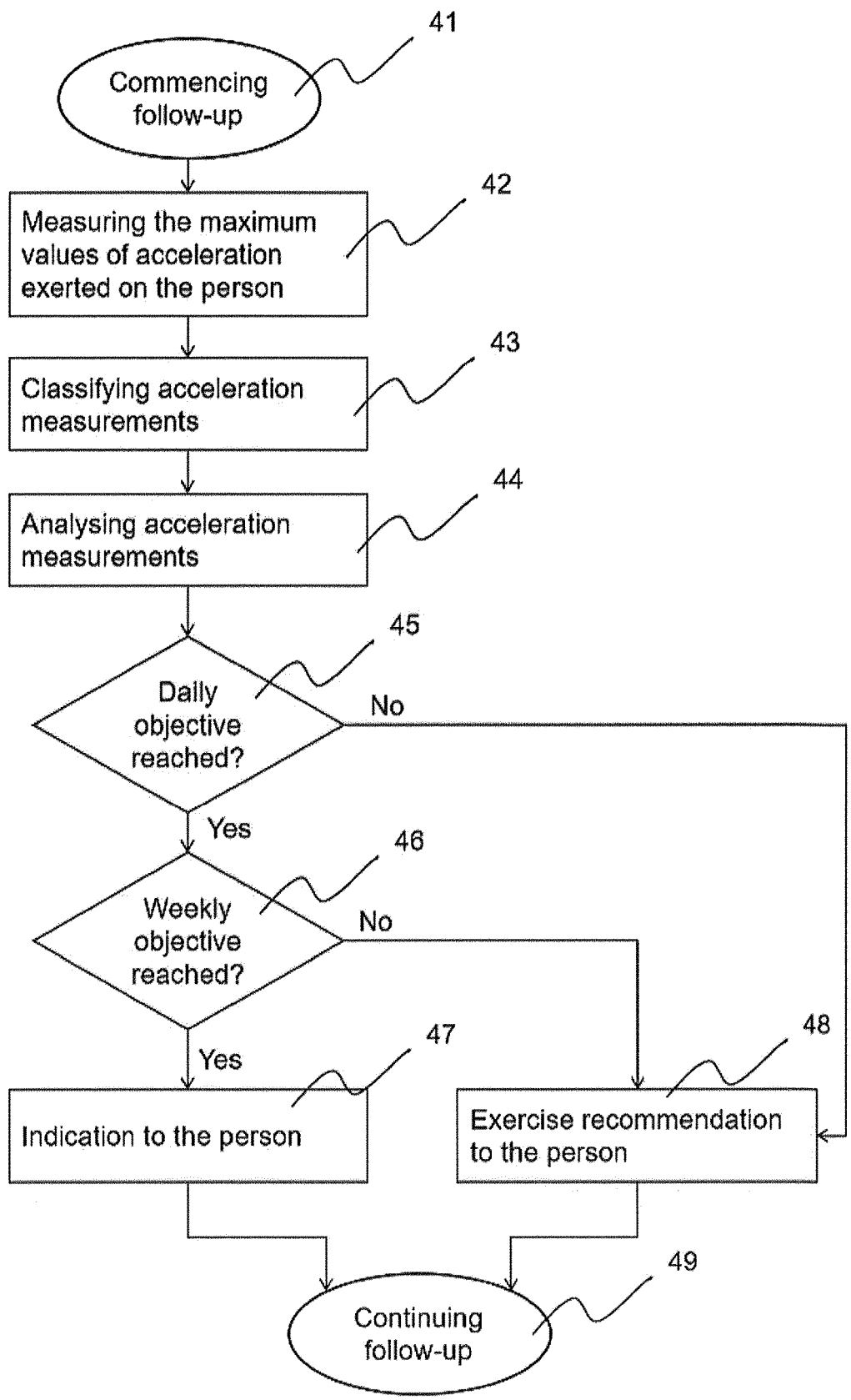
FIG. 3 is a flow-chart showing a method for defining and presenting treshold levels of physical activity to a person.
Figure 4:
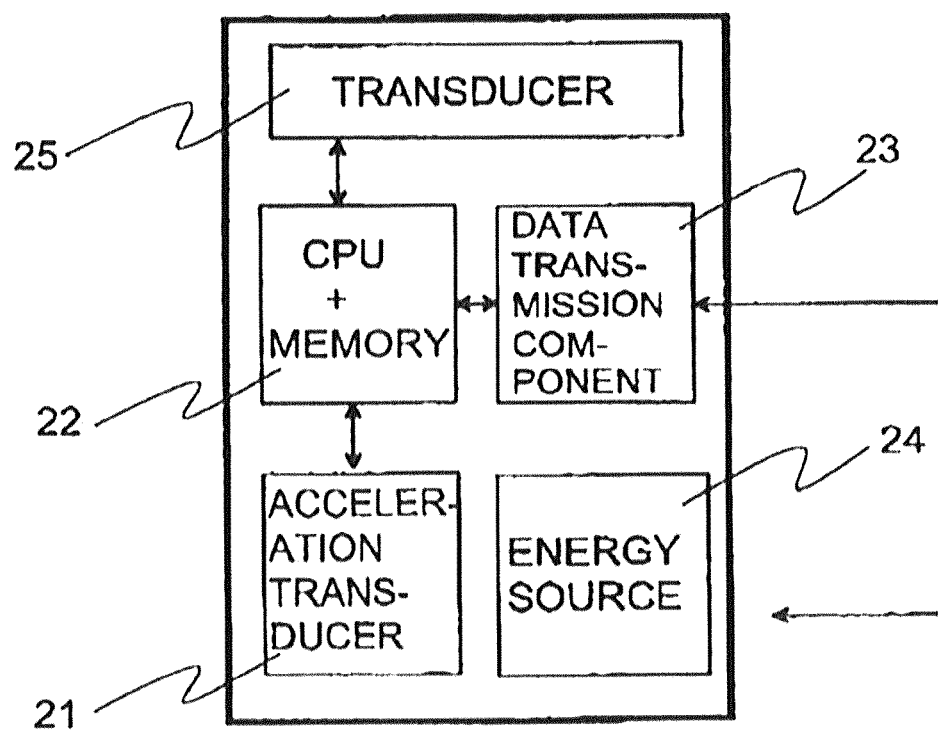
FIG. 4 is a schematic illustration fo a transducer unit to register accelelrations of the body.

Sixty-eight sedentary men and women aged 30-70 years participated in supervised exercise carrying accelerometers during wake-full time on their waist for 3 months (c.f. FIG. 2). Walking induced steps and accelerations were continuously registered reaching totally 50,000,000 data points. Exercises increased significantly number of steps or impacts in the acceleration classes 1.3-1.7 g (1 g is standing).

Figure 1:
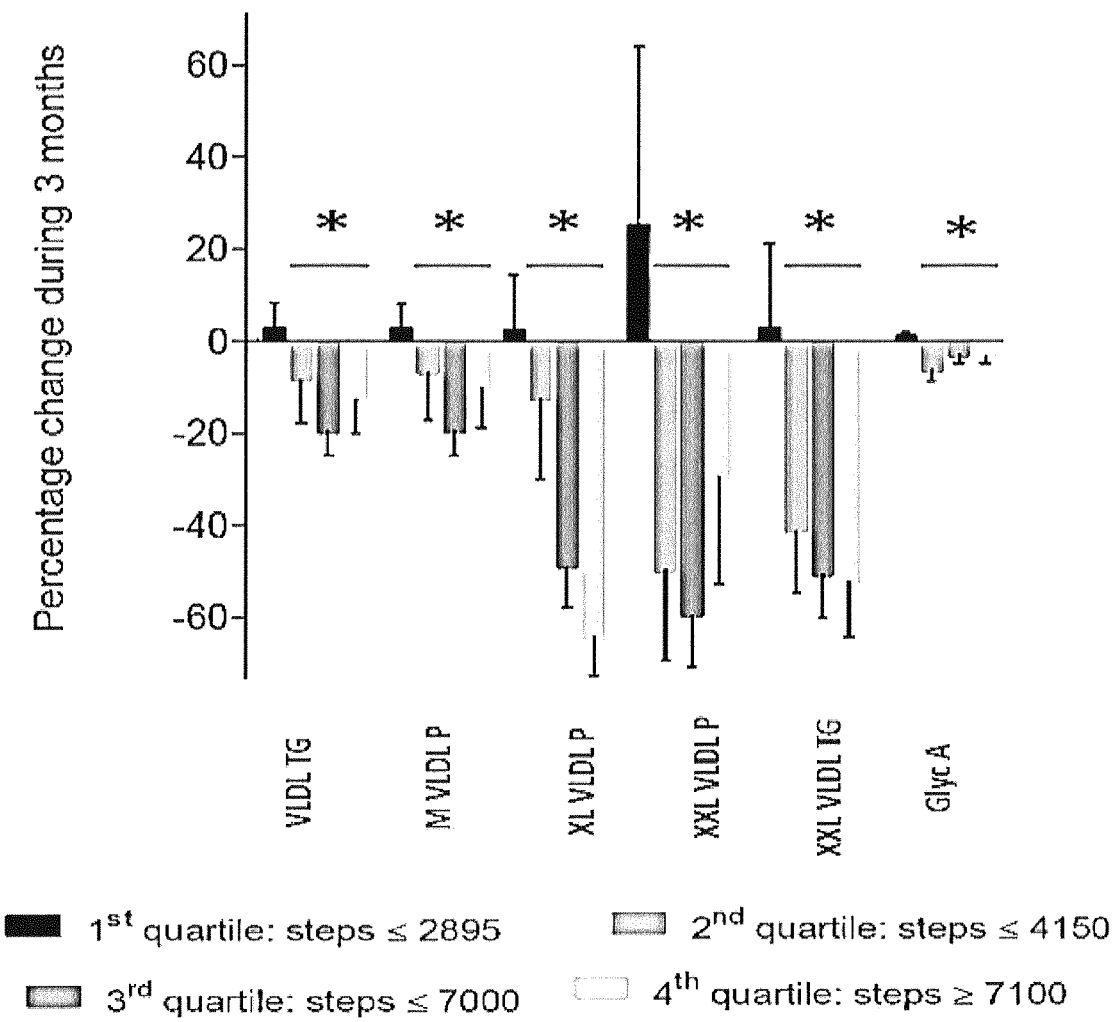

Blood samples were taken at the beginning and end of the trial to measure blood GlycA and VLDLs by an NMR method. The VLDLs measured in this invention are VLDL triglycerides (VLDL TG), medium size VLDL particles (M VLDL P), extra large VLDL particles (XL VLDL P), extremely large VLDL triglycerides (XXL VLDL TG, see FIG. 1). The steps in the acceleration class 1.3-1.7 were divided by their magnitudes to quartiles. The changes during 3 months in GlycA and VLDLs concentrations within each quartile were analyzed and were in first quartile (below 2890 daily steps) significantly higher than in the other quartiles. Therefore 2890 daily steps at 1.3-1.7 g are the thresholds for physical activity, the exceeding of which significantly reduces blood GlycA and VLDLs. This finding relates significantly to beneficial health effects of reduced levels of GlycA and VLDLs (Herzig et al. 2017 accepted for publication). Corresponding results in subjects with sedentary lifestyle have not been able to obtain by using previous methods.

The invention described herein essentially differs from the previously known methods by which exercises have been used for prevention of risk factors of diabetes, cardiovascular diseases, inflammations, cancers, dementia and premature deaths. Physicians have generally been aware about the beneficial effects of regular exercise, but the volume, intensity and duration of the exercises have remained unknown. It was novel and unexpected in our invention that in sedentary subjects physical activity of very low amount and intensity (>2890 daily steps and accelerations 1.3-1.7 g) reduced concentrations of the major risk factors of diabetes, cardiovascular diseases inflammations, cancers and early deaths. Therefore, the contents of our invention is different from those in other publications, patents and recommendations, since they do not provide information about the exact thresholds of the amounts and intensities of physical activity reducing elevated concentrations of GlycA and VLDLs known to be associated with chronic diseases and early death.

The threshold levels for daily steps and accelerations were collected from 50,000,000 data points and did not show statistically different changes during the 3 months' trial. Hence, it is not possible that new threshold levels will be needed. E.g. the WHO guidelines for physical activity were published in 2008 and the present guidelines are still similar as 19 years before. For a skilled person it is not evident to load new threshold values. High amounts of data points will make the random chance extremely low. Also the threshold levels depend on patients' physical condition, the biomarker studied and the disease to be prevented. E.g. for preventing osteoporosis appr. 50 daily steps at >4.1 g are needed but for cholesterol reduction appr. 2000 daily steps at >2.1 g are needed in healthy subjects (Vainionpää et al. 2006, Osteoporosis Int and 2007 Med Sci Sports Exerc). In sedentary subjects appr. 6500 daily steps at 1.3-1.7 g are needed to reduce cholesterol and visceral fat (Herzig et al. In J Obesity) and now 2890 daily steps at 1.3-1.7 g to reduce GlycA and VLDLs (Herzig et al. 2017 accepted for publication). It is well known that regular physical activities protects from many diseases and premature deaths but no exact biomarker threshold values for beneficial physical activities than ours presently exist.

The invention claimed is:
1. A method for defining and presenting a minimum threshold level of physical activity of a sedentary person to reduce risk of diabetes, cardiovascular diseases, inflammations, cancers and premature deaths, the method comprises:
   providing to a transducer unit reference data collected from exercising sedentary test persons exercising for a defined period of time in acceleration classes 1.3-1.7 g, wherein the reference data comprises average changes in levels of GlycA, VLDL TG, M VLDL P, XL VLDP, XXL VLDL P, and XXL VLDL TG in blood of the of test persons before and after the exercise for the defined period, and wherein the average changes are classified to four acceleration classes;

registering by the transducer unit carried by the sedentary person accelerations of the body of the sedentary person induced by a physical activity;

classifying and storing occurrence numbers (N) of registered acceleration maxima within a certain time period according to a magnitude of the maxima to one of the four acceleration classes by the transducer unit;

comparing by the transducer unit the stored occurrence numbers of the acceleration maxima of the sedentary person in each acceleration class to the reference; and identifying by the transducer unit into which physical activity class the person can be classified by using the occurrence number of acceleration maxima in the acceleration classes, wherein the method further comprises:

identifying and presenting by the transducer unit that the amount of the physical activity performed is classified to a physical activity class that corresponds with reduction of glycoprotein acyl (GlycA)-biomarker and very low density lipoprotein lipids (VLDLs) levels of persons having sedentary lifestyle when the classified acceleration counts of the sedentary person reaches a number of daily steps in the acceleration classes 1.3-1.7 g corresponding to statistically significant decrease in GlycA and VLDLs in the reference data; or a recommendation of additional physical activity is given.

2. The method according to claim 1, wherein when occurrence numbers (N) of physical activity of the person exceeds the minimum threshold value of an acceleration maxima of a particular acceleration class it is presented that the exercise performed has reduced risk of diabetes, cardiovascular diseases, inflammations, dementia, cancers and early deaths.

3. The method according to claim 2, wherein for defining the highest exercise activity class the registered acceleration maxima are divided into several acceleration classes between 1.3 g and 10 g, such as classes of 1.3<1.5 g, 1.5<1.7 g, 1.7<1.9 g, 1.9<2.1 g and >2.1 g wherein 1 g corresponds to standing.

4. The method according to claim 3, wherein each measured acceleration maxima adds to the occurrence number (N) by one in the acceleration class to which it belongs.

5. The method according to claim 4, wherein when the daily occurrence number (N) of acceleration maxima exceeds a threshold of 2890 daily steps within the acceleration classes 1.3-1.7 g, the transducer unit presents that sedentary person has performed physical activity, which has reduced GlycA and VLDLs of blood.

6. A non-transitory computer program product, comprising computer code saved on a computer readable media, which computer code are configured to execute the method of claim 1 by executing said computer program in a processor unit.

* * * * *